United States Patent
Oh

(10) Patent No.: US 11,408,848 B2
(45) Date of Patent: Aug. 9, 2022

(54) SINGLE-USE DISPOSABLE OXYGEN SENSOR

(71) Applicant: Nova Biomedical Corporation, Waltham, MA (US)

(72) Inventor: Bong Kyun Oh, Newtonville, MA (US)

(73) Assignee: NOVA BIOMEDICAL CORPORATION, Waltham, MA (US)

( * ) Notice: Subject to any disclaimer, the term of this patent is extended or adjusted under 35 U.S.C. 154(b) by 318 days.

(21) Appl. No.: 16/695,902

(22) Filed: Nov. 26, 2019

(65) Prior Publication Data

US 2021/0156814 A1   May 27, 2021

(51) Int. Cl.
| | |
|---|---|
| *G01N 27/404* | (2006.01) |
| *C08G 59/14* | (2006.01) |
| *G01N 27/31* | (2006.01) |
| *G01N 27/327* | (2006.01) |
| *G01N 27/30* | (2006.01) |
| *C08G 59/18* | (2006.01) |
| *C08F 218/08* | (2006.01) |

(52) U.S. Cl.
CPC ............ *G01N 27/31* (2013.01); *C08F 218/08* (2013.01); *C08G 59/184* (2013.01); *G01N 27/307* (2013.01); *G01N 27/327* (2013.01); *G01N 27/404* (2013.01)

(58) Field of Classification Search
CPC ... G01N 27/404; C08G 59/184; C02F 128/08; C08F 218/08
See application file for complete search history.

(56) References Cited

U.S. PATENT DOCUMENTS

| | | | |
|---|---|---|---|
| 3,718,563 A * | 2/1973 | Krull | G01N 27/404 204/415 |
| 3,800,410 A * | 4/1974 | Niedrach | G01N 27/404 29/25.03 |
| 5,514,253 A | 5/1996 | Davis et al. | |
| 7,611,621 B2 | 11/2009 | Cai et al. | |
| 7,648,624 B2 | 1/2010 | Cai et al. | |

(Continued)

FOREIGN PATENT DOCUMENTS

| | | | | |
|---|---|---|---|---|
| CN | 109762429 A * | 5/2019 | | G01N 27/12 |
| DE | 2539711 A1 * | 3/1977 | | G01N 27/58 |

OTHER PUBLICATIONS

EPO computer-generated English language translation of Muhl et al. DE 2539771 A1, downloaded Nov. 12, 2021. Patent published Mar. 17, 1977. (Year: 1977).*

(Continued)

*Primary Examiner* — Alexander S Noguerola
(74) *Attorney, Agent, or Firm* — Hayes Soloway PC

(57) ABSTRACT

An electrochemical oxygen sensor includes a sensing surface having a working electrode and a reference electrode, a hydrophilic layer formed from an oxygen diffusion-limiting layer emulsion overlaying the working electrode and a hydrophobic membrane formed from a hydrophobic solution disposed over the hydrophilic layer. The hydrophilic layer contains an epoxy network and a hydrophilic polymer. The hydrophobic layer contains an acetate copolymer and a cross-linking agent that reacts with the liquid epoxy resin in the hydrophilic layer forming the epoxy network where the hydrophobic member is water vapor and oxygen permeable.

19 Claims, 6 Drawing Sheets

(56) References Cited

U.S. PATENT DOCUMENTS 7,767,068 B2  8/2010  Lauks et al.
7,918,978 B2  4/2011  McCann et al.

OTHER PUBLICATIONS

Myers et al., "The Permeability of Polypropylene to Gases and Vapors," Journal of Polymer Science vol. XXXV, issue No. 128 (1959), pp. 285-288 (Year: 1959).*
Sun et al., Silicon Rubber with Improved Hydrophobicity, 2015 Annual report Conference on Electrical Insulation and Dielectric Phenomena, IEEE, pp. 241-244 (Year: 2015).*
EPO computer-generated English language translation of T. Cai CN 109762529 A, patent published May 17, 2019 (Year: 2019).*

* cited by examiner

SINGLE-USE DISPOSABLE OXYGEN SENSOR

BACKGROUND OF THE INVENTION

1. Field of the Invention

The present invention relates generally to a planar electrochemical sensor with membrane coatings used to perform a chemical analysis. Particularly, the present invention relates to a disposable oxygen sensor.

2. Description of the Prior Art

One of the biggest challenges in single-use sensors is making electrochemical planar oxygen sensors. Single use sensor substrate consists of a metal coated plastic substrate covered with an insulating layer. The electrode size is determined by the opening size of this layer. Usually the size of an oxygen working electrode in this format is larger than a typical electrochemical oxygen sensor and generates high current which causes sample depletion and generates erratic values when in contact with a sample. The size of the working electrode is proportional to the amount of current generated, which is based on the Cottrell equation. The Cottrell equation describes the current response, in time, as a function of a step in potential. The Cottrell equation is $$i(t) = \frac{nFAD_O^{1/2}C_O^*}{\pi^{1/2}t^{1/2}}$$

where i(t) is current, n is the number of electrons transferred in the half reaction, F is Faraday's Constant (96,485 C/mol), A is the area of the electrode, $D_O$ is the diffusion coefficient, $C_O$ is the in initial concentration, and t is time. From the equation, it is seen that as A, the area of the electrode, increases so does the i, the current.

Although it is technically possible to make a "small electrode", it is not cost effective as a single use disposable sensor.

A few different, single-use oxygen sensor technologies have been reported. One approach is from i-Stat Systems from Abbott Diagnostics. An oxygen sensor uses microfabrication technology to make a small electrode in a silicon nitride substrate. The multistep process involves masking, etching and lifting to produce a small size oxygen working electrode which is similar in size to a classic oxygen working electrode. Silicon nitride base substrates are expensive and require a complex process to produce the oxygen sensor mentioned above.

Another approach comes from Epocal, Inc., Ottawa, Ontario, Canada (an affiliate of Siemens Healthineers), where heterogeneous membranes are introduced. This membrane consists of a mixture of oil and water compartments. The mixture emulsifies a cross linkable polyvinyl alcohol aqueous media with salt and redox couple and cross linkable hydrophobic polymers to promote a manufacturing process using either dispensing or printing. The next steps require settling of the deposited layer, degassing and finally UV curing to immobilize all the compartments. This procedure is a complicated time reliant process due to the phase separation characteristics of the heterogeneous membrane, which could introduce sensor-to-sensor variations.

In another related approach, a method of determining the concentration of oxygen in a biological sample is disclosed. In U.S. Pat. No. 7,648,624 (Cai et al., 2010), there is a disclosed an oxygen sensor that includes a working electrode, a reference electrode and a reagent matrix disposed on at least the working electrode where the reagent matrix contains a reduced form of a redox mediator, an oxidase and a peroxidase to obtain an initial oxygen measurement where the oxygen sensor has a known correlation between oxygen and the predefined analyte expressed as a function of the response of the oxygen sensor to both oxygen and the predefined analyte. The process to manufacture the oxygen sensor is burdensome and time consuming, which is a function of the reagents and mixing times to provide a usable solution for dispensing onto the working electrode forming the reagent matrix.

SUMMARY OF THE INVENTION

A single use arterial blood gas (ABG) sensor has many advantages over a conventional blood gas analyzer including zero maintenance, accessibility, ease of use, reduction of contamination, cost effectiveness, quick analysis, convenience, etc.

Because a disposable oxygen sensor tends to use a comparatively large electrode surface that generates a comparatively large current compared to the oxygen electrodes found in a conventional blood-gas analyzer, an alternative method to create adequate "small current" on a large electrode is to formulate a diffusion layer that limits oxygen diffusion from the sample to the electrode. Requirements for the diffusion limiting layer are fixed path-length upon hydration, electrical conductivity and linear oxygen permeability.

In the present invention, a multi-layer reagent matrix is formed over a working electrode to create the oxygen sensor. The reagent matrix includes a hydrophilic polymer layer and a hydrophobic polymer layer. The hydrophilic polymer layer is formed by the combination of liquid epoxy resin and hydrophilic polymer emulsions where the combination is used as the oxygen diffusion limiting layer. The hydrophobic polymer layer containing epoxy curing agents are used for the cover membrane and to solidify the liquid epoxy in the hydrophilic polymer layer.

Liquid epoxy resin, including bisphenol A diglycidylether, epichlorohydrin and bisphenol A can be formed into an aqueous-epoxy emulsion by mixing it with hydrophilic polymers such as PVA, PVP etc. Epoxy is a substance that restricts oxygen diffusion while water soluble hydrophilic polymers enable oxygen dispersion and can make electrical connections in an electrochemical sensor setup. This epoxy/aqueous hydrophilic polymer mixture turns into a homogeneous emulsion which is easy to dispense and produces a homogeneous film. However, this layer can wash away once directly in contact with aqueous solution. A hydrophobic cover membrane prevents the washing away of this layer and it also allows water vapor and oxygen diffusion across the membrane. Unfortunately, if the liquid epoxy remains uncured, diffused water vapor begins to dissolve hydrophilic parts in this layer (i.e. hydration) and eventually increases the path length (i.e. the layer thickness), thereby deteriorating sensor performance.

Liquid epoxy can be cured by reacting with curing agents (e.g., amines) which turn a water miscible epoxy into a non-water soluble rigid polymer network. Epoxy-amines, however, show very fast curing reactions when contacting liquid epoxy. Once the epoxy-amines are mixed with the liquid epoxy, the reaction initiates immediately. As a result, it is very difficult to add curing agent to an epoxy/hydrophilic polymer emulsion before the dispensing process.

The present invention circumvents this problem by incorporating epoxy-amine curing agents into the hydrophobic cover membrane solution. The hydrophobic cover membrane solution also contains an acetate copolymer along with the amine curing agents. An epoxy-amine curing reaction initiates immediately after the cover membrane solution is dispensed onto the top of the epoxy/hydrophilic polymer layer. As a result of dispensing the hydrophobic cover membrane solution containing the epoxy-amine curing agent, liquid epoxy which is embedded in the hydrophilic layer emulsion turns into a rigid epoxy network containing the hydrophilic part of this layer. The rigid epoxy network formed within the diffusion layer coupled with the hydrophobic cover membrane that is formed over the diffusion layer prevents any change in the path length (i.e. the thickness) of the multi-layer reagent matrix when hydrated.

It is an object of the present invention to provide an electrochemical oxygen sensor that measures dissolved oxygen accurately in a small amount of fluid sample. It is another object of the present invention to provide an amperometric oxygen sensor that is disposable and that measures oxygen with high accuracy and precision.

The present invention achieves these and other objectives by providing, in one embodiment, an electrochemical oxygen sensor having a sensing surface with a working electrode and a reference electrode, a hydrophilic layer formed from an oxygen diffusion-limiting layer emulsion, the hydrophilic layer overlaying the working electrode where the diffusion-limiting layer contains an epoxy network and a hydrophilic polymer, and a hydrophobic membrane formed from a hydrophobic solution disposed over the hydrophilic layer, the hydrophobic solution containing an acetate copolymer and a cross-linking agent that reacts with the liquid epoxy resin in the hydrophilic layer forming the epoxy network where the hydrophobic member is water vapor and oxygen permeable.

In another embodiment of the present invention, the hydrophilic polymer is a polyvinyl alcohol.

In another embodiment of the present invention, the acetate copolymer of the hydrophobic membrane is an ethylenevinyl acetate copolymer.

In one embodiment, the epoxy network is formed by a reaction between liquid epoxy in the hydrophilic layer emulsion and the cross-linking agent from the hydrophobic layer.

In one embodiment, the electrochemical oxygen sensor is a single-use oxygen sensor.

In one embodiment, the acetate copolymer is an ethylenevinyl acetate where fifty percent (50%) of the ethylenevinyl acetate is polymerized in an ethylene vinyl polymer backbone.

In another embodiment, there is disclosed a method of forming an electrochemical oxygen sensing device. The method includes providing a sensor body having a base layer with at least two independent electrically conductive paths, an insulating and reagent holding layer disposed onto the base layer where the insulating and reagent holding layer has at least two reagent holding openings where one of the at least two reagent holding openings exposes a portion of one of the at least two independent electrically conductive paths and the other of the at least two reagent holding openings exposes a portion of another of the at least two independent conductive paths, disposing an oxygen diffusion-limiting emulsion containing a liquid epoxy and a hydrophilic polymer into one of the at least two reagent holding openings, drying the oxygen diffusion-limiting emulsion forming a hydrophilic layer, disposing a cover membrane solution containing an acetate copolymer and epoxy curing agents over the hydrophilic layer, and drying the cover membrane solution forming a hydrophobic layer.

In one embodiment of the method, the oxygen diffusion-limiting emulsion includes adding together a plurality of components that includes a predefined amount of liquid epoxy resin, a predefined amount of polyvinyl alcohol, a predefined amount of a surfactant, and a predefined amount of distilled water, and mixing the plurality of components forming an emulsion.

In another embodiment of the method, the method includes measuring 1.6 grams of the liquid epoxy resin, measuring 1.4 grams of a 10% polyvinyl alcohol, and measuring a volume of 1 milliliter of distilled water.

In one embodiment, the method further includes measuring a predefined amount of an anti-foaming agent and adding the anti-foaming agent to the hydrophilic emulsion.

In one embodiment, the method includes forming the cover membrane solution that includes adding together a plurality of cover membrane components comprising 50 wt % of an acetate copolymer, 3 wt % of epoxy curing agent, and 1 wt % of pentaerythritol tetrakis 3-mercaptopropionate, and mixing the plurality of cover membrane components in the predefined amount of THF/cyclohexanone forming the cover membrane solution.

In one embodiment, the method includes selecting 2% 2,4,6-tri(dimethylaminomethyl)phenol as the epoxy curing agent.

In one embodiment, the method further includes forming a reference electrode in another of the at least two reagent holding openings.

In another embodiment, a reagent matrix for making a working electrode into an oxygen sensor is disclosed. The reagent matrix includes a hydrophilic layer formed from an oxygen diffusion-limiting layer emulsion, the hydrophilic layer overlaying the working electrode where the diffusion-limiting layer contains an epoxy network and a hydrophilic polymer, and a hydrophobic membrane formed from a hydrophobic solution disposed over the hydrophilic layer, the hydrophobic solution containing an acetate copolymer and a cross-linking agent that reacts with the liquid epoxy resin in the hydrophilic layer forming the epoxy network where the hydrophobic member is water vapor and oxygen permeable.

In one embodiment, the epoxy network is formed by a reaction between liquid epoxy in the hydrophilic layer emulsion and the cross-linking agent from the hydrophobic layer.

DETAILED DESCRIPTION OF THE INVENTION

Figure 1:
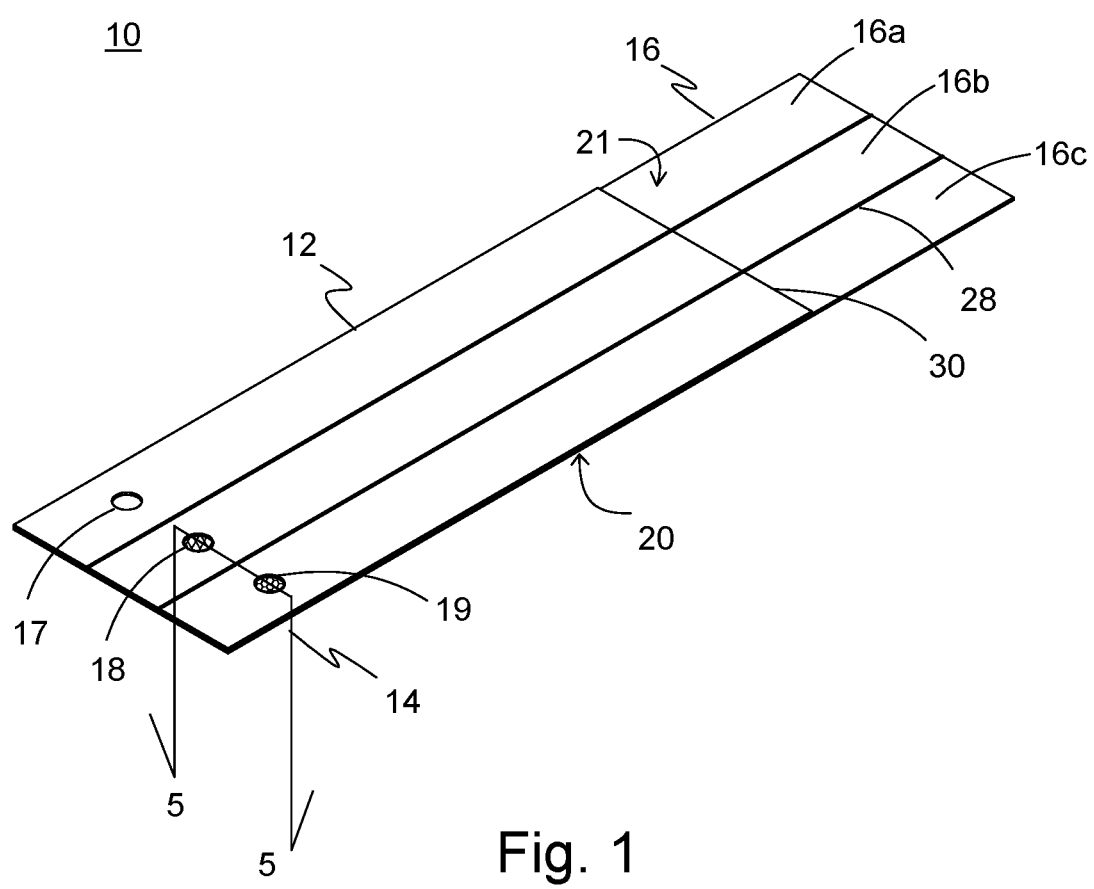
FIG. 1 is a perspective view of one embodiment of the present invention showing the oxygen sensor.

Several embodiments of the present invention are illustrated in FIGS. 1-8. In one embodiment, an oxygen sensor 10 of the present invention is made using a 2-layer construction (See FIGS. 1-4). The 2-layer construction has a laminated body 12 that includes an electrode end portion 14, an electrical contact end portion 16, at least a counter electrode 17, a working electrode 18 and a reference electrode 19 at electrode end portion 14, and electrical contact pads 16a, 16b, and 16c at electrical contact end portion 16. Laminated body 12 also includes a base layer 20, and an insulating and electrode delineating layer 30. All layers of laminated body 12 are made of a dielectric material, preferably plastic. Examples of a preferred dielectric material are polyvinyl chloride, polycarbonate, polysulfone, nylon, polyurethane, cellulose nitrate, cellulose propionate, cellulose acetate, cellulose acetate butyrate, polyester, polyimide, polypropylene, polyethylene, polystyrene, and the like.

Base layer 20 has an electrically conductive layer 21 on which is delineated at least three electrically conductive paths 22, 24 and 26. The electrically conductive paths 22, 24 and 26 may be formed by scribing or scoring electrically conductive layer 21, or by silk-screening electrically conductive paths 22, 24 and 26 onto base layer 20. Scribing or scoring of conductive layer 21 may be done by mechanically scribing the electrically conductive layer 21 creating a non-electrically conductive scoring line 28 sufficiently to create the at least three independent conductive paths 22, 24 and 26. The preferred scribing or scoring method of the present invention is done by using a carbon dioxide laser, a YAG laser or an excimer laser. Conductive layer 21 may be made of any electrically conductive material such as, for example, copper, gold, tin oxide/gold, palladium, other noble metals or their oxides, or carbon film compositions. The electrically conductive material used in this embodiment is palladium. An acceptable thickness for base layer 20 is in the range of 0.002 in (0.05 mm) to 0.010 in (0.25 mm). One such usable material for base layer 20 is a 0.005 in (0.125 mm) palladium polyester film (Stock. No. Melinex 329) sold by Marian, Inc., Indianapolis, Ind.

The insulating and electrode delineating layer 30 has at least three openings 32, 34 and 36. Opening 32 exposes a portion of conductive path 22, opening 34 exposes a portion of conductive path 24 creating reagent holding wells, and opening 36 exposes a portion of conductive path 26. In this embodiment, insulating and electrode delineating layer 30 is a medical grade one-sided adhesive tape/film available from Transcendia, Inc., Franklin Park, Ill. Acceptable thicknesses of the tape for use in the present invention are in the range of about 0.001 in. (0.025 mm) to about 0.005 in. (0.13 mm). One such tape/film, Stock No. PE31280 (about 0.002 in. (0.045 mm)), is used due to its ease of handling and good performance in terms of its ability to hold a sufficient quantity of chemical reagents and to promote capillary action through the fluid sample channel of the sensor. It should be understood that the use of a tape is not required. Insulating and electrode delineating layer 30 may be made from a plastic sheet and may be coated with a pressure sensitive adhesive, a photopolymer, ultrasonically-bonded to base layer 20, silk-screened onto base layer 20, or 3-D printed onto base layer 20 to achieve the same results as using the polyester tape mentioned.

The three openings 32, 34 and 36 define electrode areas C, W and R, respectively, forming a counter electrode C, a working electrode W, and a reference electrode R. Generally, working electrode W is loaded with a hydrophilic polymer layer deposited directly onto a portion of the conductive layer 21 exposed in electrode area W and a hydrophobic polymer layer on top of the hydrophilic polymer layer where the hydrophobic polymer layer forms a cover membrane.

The counter electrode, the working electrode and the reference electrode are each in electric contact with separate conductive paths 22, 24, and 26 respectively. The separate conductive paths terminate and are exposed for making an electric connection to a reading device on the end opposite the electrode end portion 14 of laminated body 12.

The size of the reagent holding openings is preferably made as small as possible in order to make the fluid sample channel of the oxygen sensor as short as possible while still being capable of holding sufficient chemical reagent to function properly. The shape of the reagent holding openings in this embodiment is round and has a diameter of about 0.03 in. (0.75 mm). The two reagent holding openings 32, 34 are aligned with each other and are spaced about 0.0256 in. (0.65 mm) from each other. The circular reagent holding openings are for illustrative purposes only. It should be understood that the shape of the reagent holding openings is not critical and that the size of the openings is driven more by the technical feasibility of dispensing the reagent matrix mixture into the openings and other manufacturing limitations.

The positional arrangement of the counter electrode, the working electrode, the reference electrode is not critical for obtaining usable results from the oxygen sensor. The possible electrode arrangements when the oxygen sensor is coupled with a flow cell may be C-W-R or W-C-R or any arrangement of the three electrodes, with the arrangement listed as the arrangement of electrodes would appear based on the sample flow direction across the counter electrode C, the working electrode W, and the reference electrode R. The preferred position was found to be C-W-R; that is, as the fluid sample enters the flow cell 70, the fluid sample would cover the counter electrode C first, then the working electrode W and then the reference electrode R.

Preferably, the reference electrode 19 (electrode well 36) may be loaded with a Ag/AgCl layer (e.g., by applying Ag/AgCl ink or by sputter-coating (a) a Ag layer followed by chloridizing the Ag or (b) a Ag/AgCl layer) or other reference electrode materials that do not require a redox mediator to function properly. It should be noted that the positional arrangement of the working, the reference and the counter electrodes in the channel is not critical for obtaining usable results from the sensor.

Figure 3:
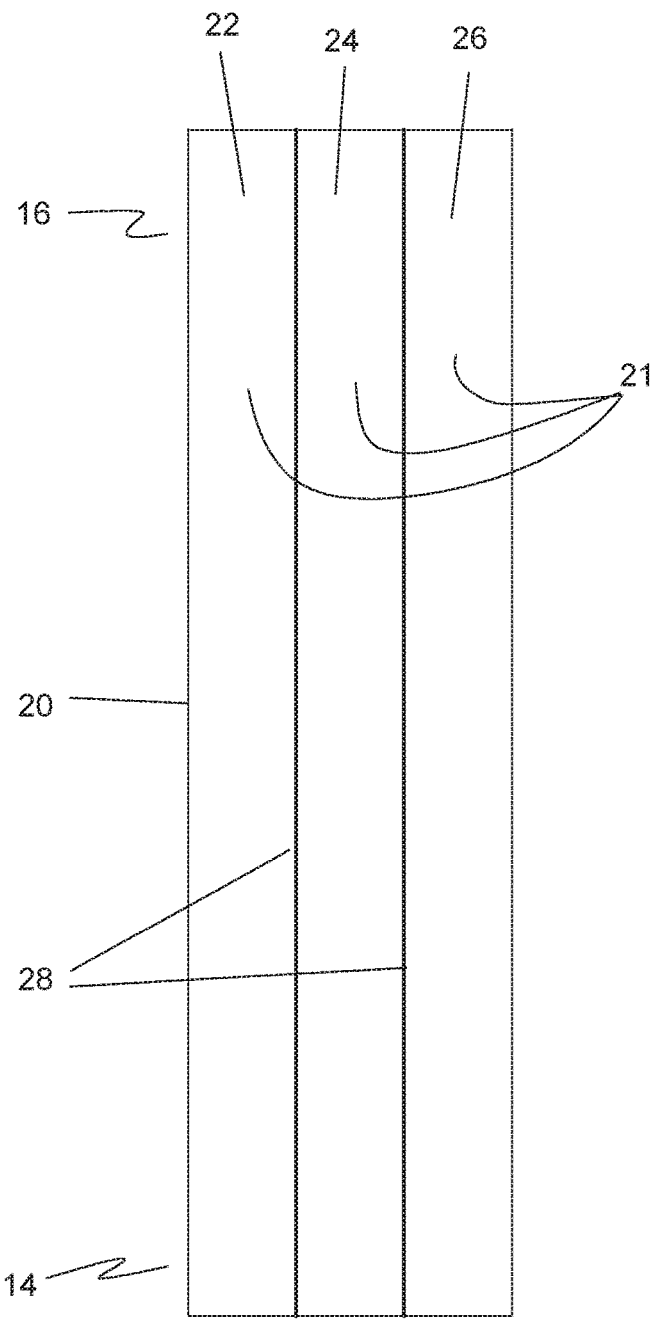
FIG. 3 is a top view of the base layer of the oxygen sensor.
Figure 4:
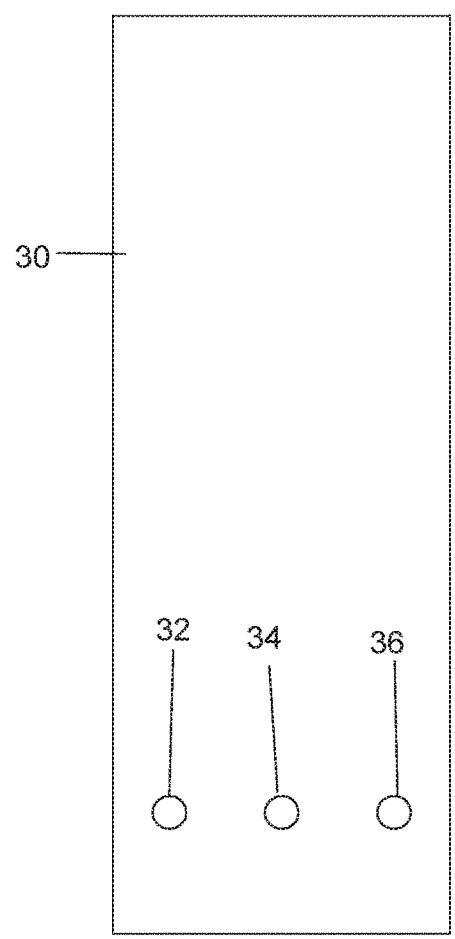
FIG. 4 is a top view of the reagent holding layer.

Turning now to FIGS. 3 and 4, there is illustrated top views of base layer 20 and insulating and reagent holding layer 30. As illustrated in FIG. 3, the symmetry of the conductive paths is such that either longitudinal end of base layer 20 may be designated as either electrode end portion 14 or electrical contact end portion 16 depending on the orientation of the insulating and reagent holding layer 30 relative to base layer 20 and the assembly process. In this embodiment, base layer 20 has scribe marks in the conductive layer 21 delineating three separate conductive paths. It should be understood that the base layer may have two or more conductive paths where the additional conductive paths may be designated for similar or other analyte sensor reagents making the oxygen sensor a multi-analyte sensor.

FIG. 4 is a top view of insulating and reagent holding layer 30. Insulating and reagent holding layer 30 has three or more openings that are spaced from each other such that each opening coincides with one of the conductive paths delineated on base layer 20. It should be understood that the electrically conductive paths disclosed herein may be made from any non-corroding metal. Carbon deposits such as for example carbon paste or carbon ink may also be used as the electrically conductive paths, all as is well known by those of ordinary skill in the art. It is further understood that the counter electrode C is used for the purpose of flowing the current from the working electrode W to the counter electrode C. Although a two electrode system may be used (i.e. a working electrode and a reference electrode), there is a disadvantage when using a relatively large working electrode as in this case compared to conventional oxygen sensors. The issue is that the reference electrode in an amperometric system is required to maintain a high charge density. In the case where a high current flow from the working electrode to the reference electrode exists in a two electrode system, the Ag—AgCl reference electrode could deteriorate due to a changing current density. This, in turn, would cause a bias potential window shift and inaccuracy in the determined oxygen concentration level.

Figure 5:
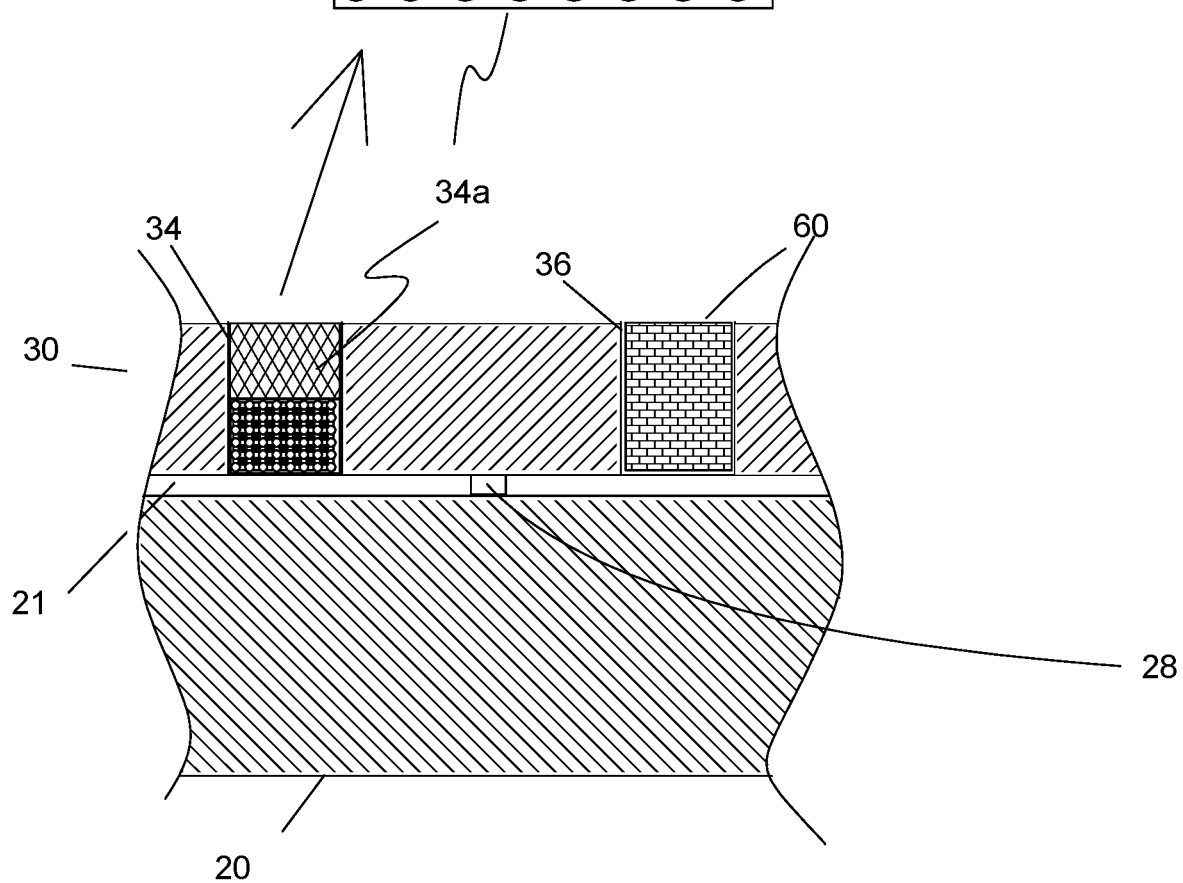
FIG. 5 is an enlarged, cross-sectional view of the oxygen sensor taken along line 5-5 in FIG. 1.

Turning now to FIG. 5, there is illustrated an enlarged, cross-sectional view of the oxygen sensor 10 taken along line 5-5 in FIG. 1. It should be understood that the relative sizes of the layers 20, 30, the electrode wells 32, 34, 36 and the thicknesses of the working electrode reagent matrix and the reference electrode reagent matrix are not to size but merely to illustrate the various components of oxygen sensor 10. As seen in FIG. 5, base layer 20 has electrically conductive layer 21 disposed there on with scoring lines 28 creating a non-electrically conductive break in conductive layer 21. Insulating and reagent holding layer 30 has reagent holding opening 34 containing the working electrode oxygen-diffusion limiting, multi-layer reagent matrix 34a and reagent holding opening 36 containing the reference electrode reagent matrix 60.

Figure 6:
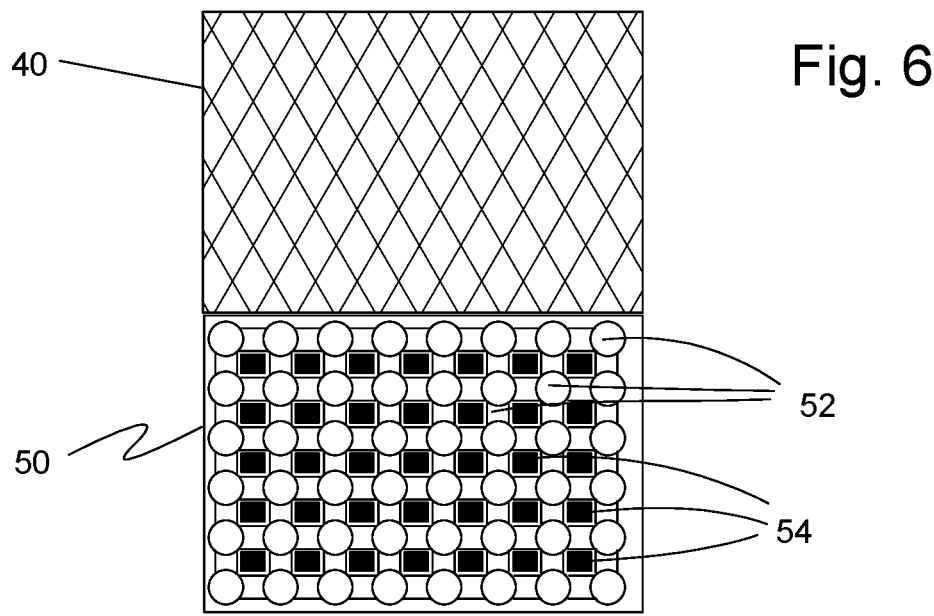
FIG. 6 is an enlarged view of the multi-layer reagent matrix of the working electrode showing the hydrophilic layer and the hydrophobic layer.

FIG. 6 is an enlarged view of multi-layer reagent matrix 32a. Multi-layer reagent matrix 32a includes a hydrophilic polymer layer 50 and a hydrophobic polymer layer 40. Hydrophilic layer 50 includes an epoxy network 52 and a hydrophilic portion 54. Hydrophobic layer 40 is, as the name implies, is not water soluble but is water vapor and oxygen permeable.

The polymer used as the hydrophilic portion in the hydrophilic layer should be sufficiently water-soluble and should also be capable of stabilizing all other chemicals in the reagent to the conductive surface layer in the electrode area. Suitable polymers include, but are not limited to, low and high molecular weight polyethylene oxide (PEO), polyethylene glycol, polyvinyl pyrrolidone (PVP), starch, methylcellulose, hydroxypropylcellulose, polyvinyl alcohol (PVA), carboxy methyl cellulose (CMC), and polyamino acids. The hydrophilic portion may be a single polymer or a combination of polymers preferable in a concentration range of about 0.02% (w/w) to about 7.0% (w/w). The preferred hydrophilic portion in the hydrophilic layer of the present invention is PVA. PVA is available from Scientific Polymer Products, NY, USA.

The hydrophilic layer also contains an epoxy network that is not water soluble. The epoxy network, however, is created from a hydrophilic emulsion containing a water-soluble, liquid epoxy resin.

The polymer used in the hydrophobic layer is an ethylenevinyl acetate copolymer. It is a 50 wt % vinyl acetate available from Scientific Polymer Products, NY, USA.

A surfactant may be optionally included in the hydrophilic emulsion (used to create the hydrophilic layer) to facilitate dispensing of the hydrophilic emulsion into the working electrode area W. The surfactant also helps in quickly dissolving the dry chemical reagents (i.e. the PVA) when a fluid enters the sample chamber 17 of the oxygen sensor 10, 430. The amount and type of surfactant is selected to assure the previously mentioned functions. Surfactants can be selected from, but are not limited to, various anionic, cationic, non-ionic, and zwitterionic detergents. Examples of acceptable surfactants are polyoxyethylene ether, Tween 20, sodium cholate hydrate, hexadecylpyridinium cholide monohydrate and CHAPs. The preferred surfactant is a polyoxyethylene ether. More preferably, it is t-octylphenoxypolyethoxyethanol and is available under the brand name Triton X-100 from Sigma-Aldrich. The concentration of surfactant in the reagent matrix is preferably about 0.01% (w/w) to about 2%.

Figure 7:
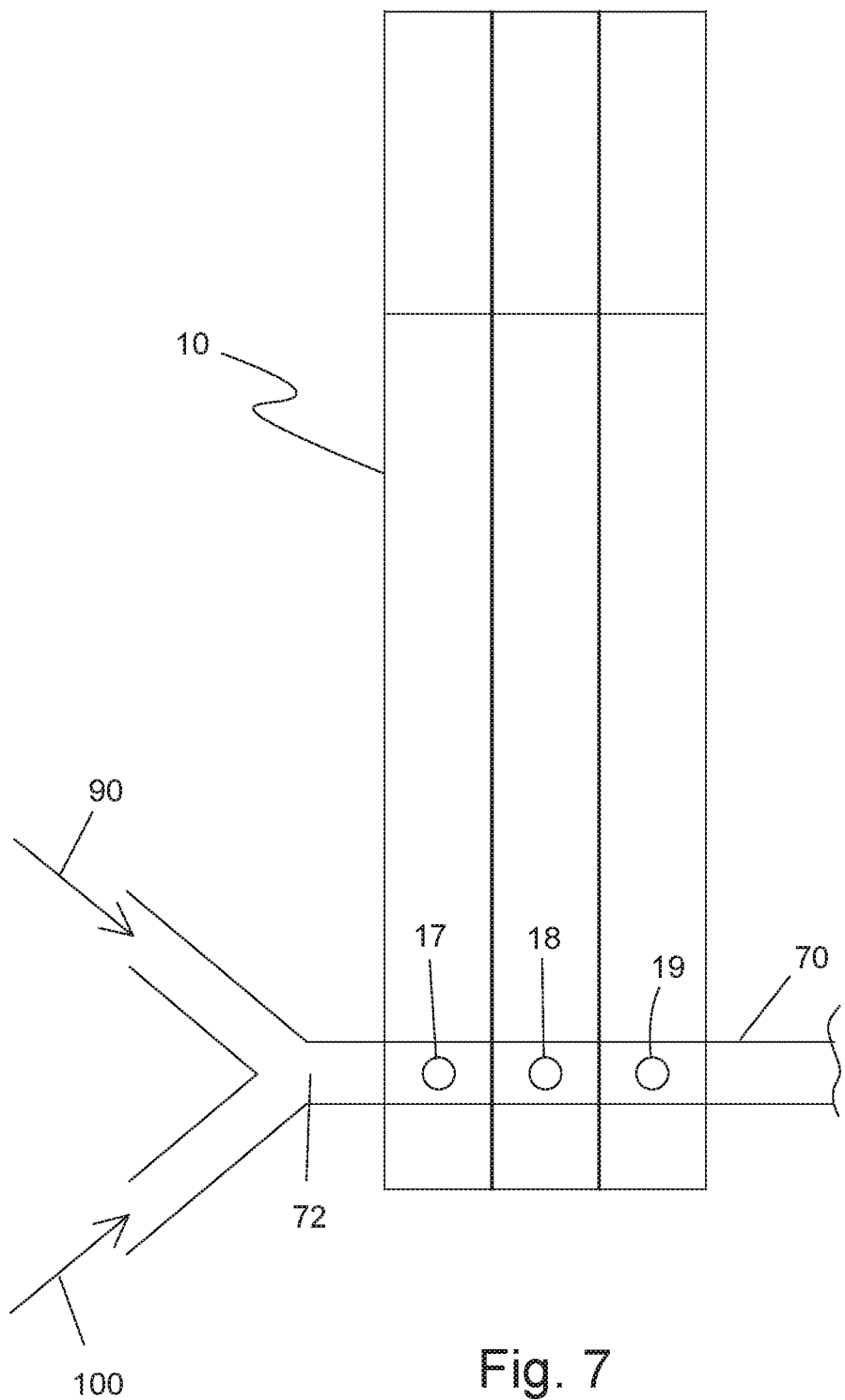
FIG. 7 is an illustrative top view of the oxygen sensor connected to a flow cell.

FIG. 7 is a top view illustration showing the oxygen sensor 10 connected to a flow cell 70. Flow cell 70 has a test chamber 74 in which working electrode 18 and reference electrode 19 are disposed. Test chamber 74 has a test chamber inlet 72 connected to a calibrant supply line 90 and a blood sample supply line 100. A predefined amount of calibrant is supplied to test chamber 74 for a one-point calibration. After calibration, the calibrant is moved out of test chamber 74 followed by a predefined amount of blood sample. The blood sample is measured for the amount of oxygen (i.e. the oxygen concentration) in the blood sample. It is understood that the oxygen sensor 10 is electrically connected to proper electronics to perform the chronoamperometric measurement.

Preparation of the Hydrophilic and Hydrophobic Layer Compositions

The preferred reagent layer composition for the hydrophilic emulsion used to create the hydrophilic layer is preferably prepared in two steps, although it may be prepared in one step:

Step 1: Adding together 1.6 gm of liquid epoxy resin available under the trademark D.E.R. 331 from The Dow Chemical Company (DER 331), 1.4 g of 10% polyvinyl alcohol (Mw. 130K), 1% Triton X-100 and 1 ml of distilled water, and 100 mg of an anti-foaming agent.

Step 2: Mixing all the components in Step 1 above using a homogenizer at 9,000 rpm for 1 minute. The prepared hydrophilic emulsion is stable for several days when stored at room temperature Reagent layer composition for the cover membrane solution used to create the hydrophobic layer is also preferably prepared in two steps although it too may be prepared in one step:

Step 1: Adding 2 wt % ethylenevinyl acetate copolymer where the copolymer is an ethylenevinyl acetate where 50% acetate is copolymerized in ethylenevinyl polymer backbone, 3% epoxy curing agents (2% 2,4,6-tri(dimethylaminomethyl)phenol, and 1% pentaerythritol tetrakis(3-mercaptopropionate)) in THF/Cyclohexanone.

Step 2: Mixing the ingredients in Step 1 together forming the cover membrane solution. The prepared cover membrane solution is stable for several weeks stored at room temperature.

Sensor Construction

Assembly of the various embodiments of the present invention is relatively straightforward. Generally, the base layer and insulating and reagent holding layer are laminated to each other followed by dispensing the appropriate reagent mixture into each of the reagent holding openings.

Figure 2:
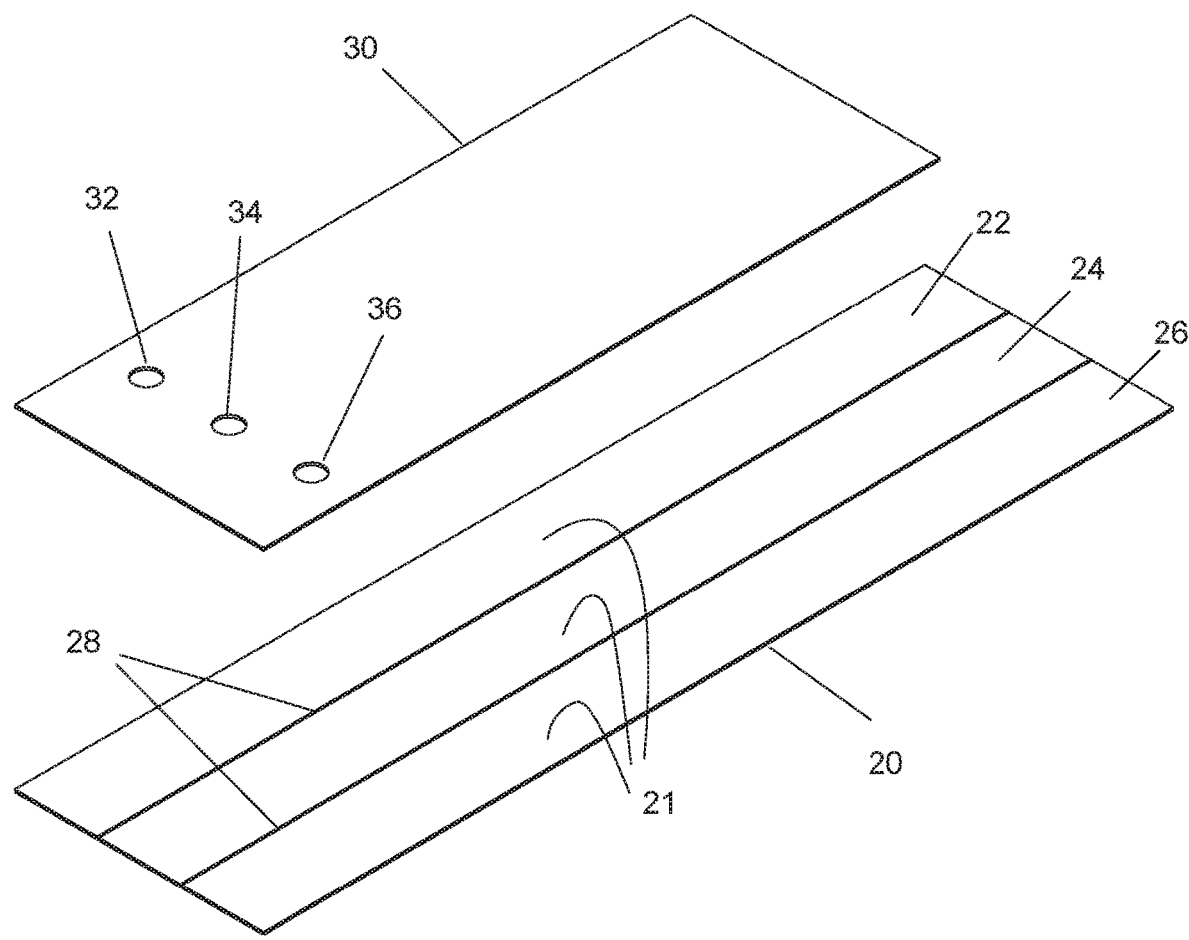
FIG. 2 is an exploded view of the embodiment in FIG. 1 showing the two component layers of the oxygen sensor.

More particularly for the 2-layer configuration shown in FIG. 1, a piece of a palladium film is cut to shape as illustrated in FIG. 2 forming base layer 20 of sensor 10. Even though mechanical scribing is an option, a laser is preferably used to score the conductive palladium polyester film. As illustrated in FIG. 2, the film is scored by the laser such that three electrode areas at sample fluid end 14 and three contact points 22, 24 and 26 are formed at electrical contact end 16. The scoring line is very thin but sufficient to create three separate and distinct electrically conductive paths. A piece of one-sided adhesive tape is then cut to size and shape, forming insulating and electrode delineating layer 30 so that it will cover a major portion of conductive layer 21 of base layer 20 except for exposing a small electrical contact area illustrated in FIG. 1 by reference number 16.

Before attaching insulating and electrode delineating layer 30 to base layer 20, at least three openings 32, 34 and 36 of substantially equal size are punched by laser, or by mechanical means such as a die-punch assembly, creating electrode openings 32, 34 and 36 in insulating and electrode delineating layer 30. The shape of the electrode openings may be any shape. In the illustrated embodiment, the openings are circular. The preferred hole size for openings 32 and 34 has a typical diameter of about 0.030 in. (0.75 mm) but may be any size. As illustrated in FIG. 2, electrode openings 32 and 34 (and optional electrode opening 36 when included) are aligned with each other and have a spacing of about 0.020 in. (0.508 mm) to about 0.050 in. (1.27 mm) between adjacent openings. The circular openings are for illustrative purposes only. It should be understood that the shape and size of the openings or the distance between them is not critical. The circular openings do not have to be substantially equal in size so long as the ratio of the surface areas remains substantially constant. Although the arrangement of the electrodes may be any combination, the preferred arrangement of the electrodes formed in openings 32, 34 and 36 is C (counter electrode), W (working electrode) and R (reference electrode) as positioned from the test chamber inlet 72. Insulating and electrode delineating layer 30 is then attached to base layer 20 in such a way as to define the electrode wells for creating counter electrode C, working electrode W and reference electrode R.

A predefined amount of hydrophilic emulsion is dispensed into the working electrode well and dried. For example, it may be air dried for several minutes at room temperature or dried for thirty seconds at 37° C. forming the hydrophilic layer. Drying for a shorter time period at a temperature above room temperature allows for a more efficient manufacturing process. The hydrophilic emulsion and its composition is as described above.

Next, the cover membrane solution is dispensed onto the hydrophilic layer so that the solution completely covers the hydrophilic layer and either air dried overnight at room temperature or dried for 30 seconds or more at 37° C. During this process, the epoxy curing agents in the cover membrane solution react with the liquid epoxy resin in the hydrophilic layer forming a rigid epoxy network containing the hydrophilic portions of the layer (i.e. polyvinyl alcohol), where the epoxy network maintains a predefined path length (i.e. thickness) of the hydrophilic layer when the hydrophilic layer is hydrated by calibrant. As discussed previously, the hydrophobic layer allows diffusion of water vapor and oxygen across the cover membrane while the hydrophilic layer is an oxygen diffusion-limiting layer that contains water soluble hydrophilic polymers, which enables oxygen dispersion and makes electrical connections to the working electrode.

The length of time required to dry the reagents is dependent on the temperature at which the drying process is performed.

Testing the Oxygen Sensor

The oxygen sensor 10 was connected to a flow cell as illustrated in FIG. 7. When a fluid sample is applied to an oxygen sensor of the embodiment of the present invention shown in FIG. 1, the fluid sample enters the flow cell 70 and flows over electrodes C, W, and R and is stopped for a predefined period of time. The length of time depends on whether the fluid is the calibrant or a blood sample.

Chronoamperometry was used to measure the current response of the oxygen sensor 10 using a Nova Biomedical blood gas analyzer but a potentiostat could also be used. The oxygen sensor made like those shown in FIG. 1 and described above were used to test the response of the oxygen sensor 10 of the present invention to the concentration of oxygen in the sample. A blood sample containing a predefined amount of oxygen is applied to the sample inlet 18 of the sensor strip and enters the sensor strip while a potential of −0.10 V to −0.70 volts (depending on reference electrode used) is applied between the working electrode and the reference electrode. In the particular examples described here, the applied potential was −0.65 V versus a Ag—AgCl reference electrode. The output response current is proportional to the concentration in the blood sample. When using the Nova Biomedical blood gas analyzer, the measurements values were given as the partial pressure of oxygen in mmHg.

Example 1

Demonstration of Reference $pO_2$ versus Sensor $pO_2$ measured at Different Levels of $pO_2$ Blood samples with different $pO_2$ were tested with the oxygen sensor of the present invention using the Nova Biomedical pHOx blood gas analyzer. In the alternative, an Electrochemical Analyzer (CH Instruments, Model 812, Austin, Tex., USA) may also be used to measure the current response directly from the oxygen sensor strips 10. Oxygen concentration ($pO_2$) was controlled using a Tonometer (Precision Gas Mixer, PGM-3, Medicor, Inc., Salt Lake City, Utah, USA). Two milliliters of the blood sample were placed into a temperature-controlled (37° C.) cylindrical rotating cuvette and tonometered for 15 minutes.

A one-point calibration before measuring a blood sample is required to hydrate the hydrophilic layer and to establish a reference point for the oxygen sensor 10. The one-point calibrant used was 110 mmHg $pO_2$ solution. The one-point calibrant is flowed through the flow cell to each oxygen sensor and allowed to stay in the flow cell for 90 seconds to hydrate the hydrophilic layer. At the end of the 90-second hydration period, the one-point calibration measurement is performed. Following the calibration, a tonometered blood sample was introduced to the oxygen sensor replacing the calibrant and a reading was taken 30 seconds after introducing the blood sample. The concentration calculation was based on the one-point calibration and using the Cottrell equation. When done in this fashion, it was found that the $pO_2$ measured responses are linear over a range of 50 mm Hg to 170 mm Hg $pO_2$ at the working electrode. Six blood samples with tonometered oxygen levels in a range of 49 mmHg to 243 mmHg were tested. The tonometered blood samples were also measured with the Nova Biomedical pHOx blood gas analyzer to obtain a reference reading for each blood sample for comparison with the readings obtained from the oxygen sensor of the present invention.

In this example, multiple biosensors using the palladium substrate were made for testing the response of the oxygen sensor. The results are shown in Table 1.

TABLE 1

| Blood Level | pHOx pO2, mmHg | Sensor pO2, mmHg | Sensor SD |
|---|---|---|---|
| L1 | 49.0 | 44.7 | 8.4 |
| L2 | 82.0 | 81.5 | 5.0 |
| L3 | 103.0 | 96.3 | 5.2 |
| L4 | 122.0 | 130.8 | 3.3 |
| L5 | 167.0 | 157.0 | 9.0 |
| L6 | 243.0 | 183.0 | 12.7 |

Each blood level was tested at least ten (10) times (i.e. using 10 disposable oxygen sensors 10 for each oxygen concentration level and the average value calculated and displayed in Table 1. The standard deviation value for each concentration level tested is also provided.

Figure 8:
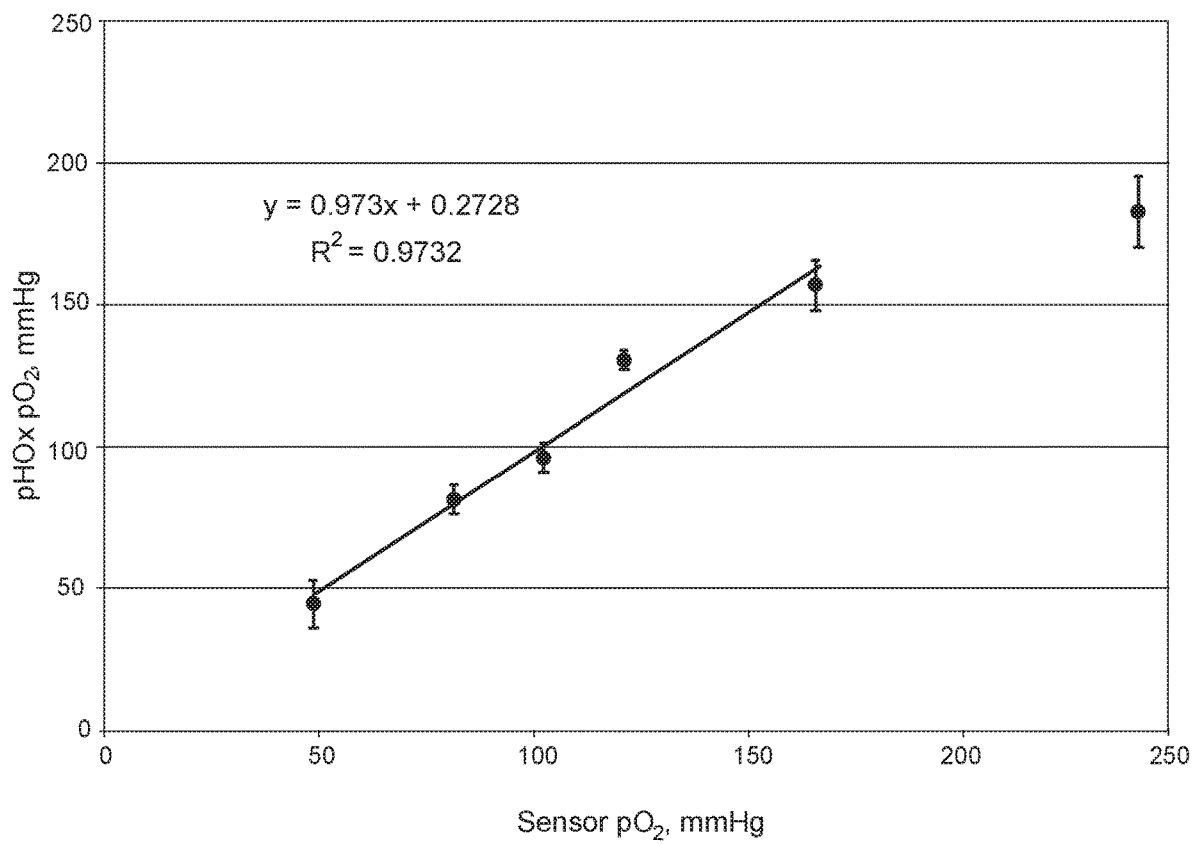
FIG. 8 is a graphic illustration showing the correlation between the readings of the oxygen sensor of the present invention and the readings from a blood gas analyzer using tonometered blood samples.

FIG. 8 shows the measured $pO_2$ response of the working electrode of the present invention (i.e. the hydrophilic layer/cover membrane layer electrode) to varying $pO_2$ levels of 49 mmHg, 82 mmHg, 103 mmHg, 122 mmHg, 167 mmHg, and 243 mmHg. The responses (i.e. current responses) are linear to the oxygen concentration throughout the first five $pO_2$ ranges mentioned above.

The advantages of the present invention over a conventional blood gas analyzer includes zero maintenance, accessibility, ease of use, reduction of contamination, cost effectiveness, quick analysis, convenience, etc.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. An electrochemical oxygen sensor comprising:
   a sensing surface having a working electrode and a reference electrode;
   a hydrophilic layer formed from an oxygen diffusion-limiting layer emulsion, the hydrophilic layer overlaying the working electrode wherein the hydrophilic layer contains an epoxy network and a hydrophilic polymer; and
   a hydrophobic membrane formed from a hydrophobic solution disposed over the hydrophilic layer, the hydrophobic solution containing an acetate copolymer and a cross-linking agent that reacts with the epoxy network, wherein the hydrophobic membrane is water vapor and oxygen permeable.

2. The electrochemical oxygen sensor of claim 1 wherein the hydrophilic polymer is a polyvinyl alcohol.

3. The electrochemical oxygen sensor of claim 1 wherein the acetate copolymer of the hydrophobic membrane is an ethylenevinyl acetate copolymer.

4. The electrochemical oxygen sensor of claim 3 wherein the acetate copolymer is an ethylenevinyl acetate where fifty percent of the ethylenevinyl acetate is polymerized in an ethylene vinyl polymer backbone.

5. The electrochemical oxygen sensor of claim 1 wherein the epoxy network is formed by a reaction between liquid epoxy in the hydrophilic layer emulsion and the cross-linking agent from the hydrophobic layer.

6. The electrochemical oxygen sensor of claim 1 is a single-use oxygen sensor.

7. A method of forming an electrochemical oxygen sensor comprising:
   providing a sensor body having a base layer with at least two independent conductive paths, and an insulating and reagent holding layer disposed onto the base layer wherein the insulating and reagent holding layer has at least two reagent holding openings wherein one of the at least two reagent holding openings exposes a portion of one of the at least two independent conductive paths and the other of the at least two reagent holding openings exposes a portion of another of the at least two independent conductive paths;
   disposing an oxygen diffusion-limiting emulsion containing a liquid epoxy and a hydrophilic polymer into one of the at least two reagent holding openings;
   drying the oxygen diffusion-limiting emulsion forming a hydrophilic layer;
   disposing a cover membrane solution containing an acetate copolymer and an epoxy curing agent over the hydrophilic layer; and
   drying the cover membrane solution forming a hydrophobic layer,
   wherein the one of the at least two reagent holding openings containing the hydrophilic layer and the hydrophobic layer forms a working electrode.

8. The method of claim 7 further comprising forming the oxygen diffusion-limiting emulsion comprising:
   adding together a plurality of components comprising a predefined amount of liquid epoxy resin, a predefined amount of polyvinyl alcohol, a predefined amount of a surfactant, and a predefined amount of distilled water; and
   mixing the plurality of components forming an emulsion.

9. The method of claim 8 further comprising:
   measuring 1.6 grams of the liquid epoxy resin;
   measuring 1.4 grams of a 10% polyvinyl alcohol; and
   measuring a volume of 1 milliliter of distilled water.

10. The method of claim 8 further includes adding a predefined amount of an anti-foaming agent to the oxygen diffusion-limiting emulsion.

11. The method of claim 7 further comprising forming the cover membrane solution comprising:
   adding together a plurality of cover membrane components comprising 50 wt % of an acetate copolymer, 3 wt % of the epoxy curing agent, and 1 wt % of pentaerythritol tetrakis 3-mercaptopropionate; and
   mixing the plurality of cover membrane components in an amount of THF/cyclohexanone forming the cover membrane solution.

12. The method of claim 11, wherein the epoxy curing agent is 2% 2,4,6-tri(dimethylaminomethyl)phenol.

13. The method of claim 7 further comprising forming a reference electrode in another of the at least two reagent holding openings.

14. A multi-layer reagent matrix for making a working electrode into an oxygen sensor, the reagent matrix comprising:
   a hydrophilic layer formed from an oxygen diffusion-limiting layer emulsion containing a liquid epoxy resin, the hydrophilic layer overlaying a working electrode wherein the hydrophilic layer contains an epoxy network and a hydrophilic polymer; and a hydrophobic membrane formed from a cover membrane solution disposed over the hydrophilic layer, the cover membrane solution containing an acetate copolymer and a cross-linking agent that reacts with the liquid epoxy resin in the hydrophilic layer forming the epoxy network, wherein the hydrophobic membrane is water vapor and oxygen permeable.

15. The reagent matrix of claim 14 wherein the hydrophilic polymer is a polyvinyl alcohol.

16. The reagent matrix of claim 14 wherein the acetate copolymer of the hydrophobic membrane is an ethylenevinyl acetate copolymer.

17. A method of making a multi-layer reagent matrix that transforms a working electrode into an oxygen sensor, the method comprising:
   forming an oxygen diffusion-limiting emulsion for depositing onto a surface of a working electrode, the oxygen diffusion-limiting emulsion includes adding together a plurality of components comprising a predefined amount of liquid epoxy resin, a predefined amount of polyvinyl alcohol, a predefined amount of a surfactant, and a predefined amount of distilled water, and mixing the plurality of components forming an emulsion; and
   forming a cover membrane solution for depositing onto the oxygen diffusion-limiting emulsion after the oxygen diffusion-limiting emulsion is dried, wherein forming the cover membrane solution includes adding together a plurality of cover membrane components comprising a predefined amount of an acetate copolymer, a predefined amount of an epoxy curing agent, and a predefined amount of pentaerythritol tetrakis 3-mercaptopropionate, and mixing the plurality of cover membrane components in a predefined amount of THF/cyclohexanone,
   wherein the oxygen diffusion-limiting emulsion is used to create a hydrophilic layer on the working electrode and wherein the cover membrane solution is used to create a hydrophobic layer on the hydrophilic layer.

18. The method of claim 17 wherein the predefined amount of liquid epoxy resin is 1.6 grams, the predefined amount of polyvinyl alcohol is 1.4 grams, and the predefined amount of distilled water is 1 milliliter.

19. The method of claim 17 wherein the predefined amount of the acetate copolymer is 50 wt %, the predefined amount of the epoxy curing agent is 3 wt %, and the predefined amount of pentaerythritol tetrakis 3-mercaptopropionate is 1 wt %.

\* \* \* \* \*